United States Patent
Mazzucco et al.

(10) Patent No.: US 9,700,324 B2
(45) Date of Patent: Jul. 11, 2017

(54) SURGICAL CLIP APPLICATOR

(71) Applicant: ZSX Medical, LLC, Philadelphia, PA (US)

(72) Inventors: Dan Mazzucco, Haddon Heights, NJ (US); Robert S. Cargill, II, West Deptford, NJ (US); Todd J. Kent, Cherry Hill, NJ (US); David George Reed, Langhorne, PA (US); Binh Bao Vu, Bristol, PA (US); Eric Sugalski, West Chester, PA (US); David Schoon, Philadelphia, PA (US); Jesse Butch, Philadelphia, PA (US); Ryan Meers, West Chester, PA (US); Julian Trowbridge, Philadelphia, PA (US)

(73) Assignee: ZSX Medical, LLC, Philadelphia, PA (US)

( * ) Notice: Subject to any disclaimer, the term of this patent is extended or adjusted under 35 U.S.C. 154(b) by 129 days.

(21) Appl. No.: 14/597,798

(22) Filed: Jan. 15, 2015

(65) Prior Publication Data
US 2015/0196302 A1    Jul. 16, 2015

Related U.S. Application Data

(60) Provisional application No. 61/928,171, filed on Jan. 16, 2014.

(51) Int. Cl.
*A61B 17/12*    (2006.01)
*A61B 17/128*    (2006.01)
(Continued)

(52) U.S. Cl.
CPC ........ *A61B 17/1285* (2013.01); *A61B 17/122* (2013.01); *A61B 2017/2939* (2013.01)

(58) Field of Classification Search
CPC ... A61B 17/1285; A61B 17/122; A61B 17/10; A61B 17/068; A61B 17/0682;
(Continued)

(56) References Cited

U.S. PATENT DOCUMENTS 5,100,420 A * 3/1992 Green ................ A61B 17/1285
227/19
5,358,506 A * 10/1994 Green .................... A61B 17/29
227/181.1

(Continued)

*Primary Examiner* — Alexander Orkin
(74) *Attorney, Agent, or Firm* — Panitch Schwarze Belisario & Nadel LLP

(57) ABSTRACT

A surgical clip applicator includes a base housing having a body portion, a movable trigger, a cannula, and a clip application mechanism extending within and through at least a portion of a length of the cannula. The clip application mechanism includes a movable first linkage and a jaw rotatable about a pivot mount. A first actuation of the trigger causes the first linkage to be moved in a linear direction with respect to the body portion and the cannula and the jaw to be rotated in a first direction about the pivot mount, for placing the clip in an open position on the patient's tissue. A second actuation of the trigger causes the jaw to be rotated in second direction about the pivot mount, the second direction being opposite to the first direction, placing the clip in a closed position on the patient's tissue.

12 Claims, 15 Drawing Sheets

(51) Int. Cl.
*A61B 17/122* (2006.01)
*A61B 17/29* (2006.01)

(58) Field of Classification Search
CPC ............ A61B 17/0684; A61B 17/0686; A61B 2017/2939; A61B 2017/2941
See application file for complete search history.

(56) References Cited

U.S. PATENT DOCUMENTS

| | | | | |
|---|---|---|---|---|
| 5,433,721 | A * | 7/1995 | Hooven | A61B 17/072 227/175.1 |
| 5,609,599 | A * | 3/1997 | Levin | A61B 17/083 606/151 |
| 5,681,330 | A * | 10/1997 | Hughett | A61B 17/1285 227/901 |
| 6,716,232 | B1 * | 4/2004 | Vidal | A61B 17/07207 227/176.1 |
| 2002/0068946 | A1 * | 6/2002 | Kortenbach | A61B 1/00073 606/142 |
| 2003/0023249 | A1 * | 1/2003 | Manetakis | A61B 17/1285 606/139 |
| 2007/0093856 | A1 * | 4/2007 | Whitfield | A61B 17/1285 606/142 |
| 2007/0213747 | A1 * | 9/2007 | Monassevitch | A61B 17/0643 606/151 |
| 2008/0234705 | A1 * | 9/2008 | Cropper | A61B 17/128 606/157 |
| 2012/0022584 | A1 * | 1/2012 | Donnigan | A61B 17/29 606/206 |

* cited by examiner

SURGICAL CLIP APPLICATOR

CROSS-REFERENCE TO RELATED APPLICATIONS

This application claims priority to U.S. Provisional Patent Application No. 61/928,171, filed on Jan. 16, 2014, entitled "Surgical Clip Applicator," the entire contents of which are incorporated by reference herein.

BACKGROUND OF THE INVENTION

Embodiments of the present invention relates generally to surgical clip applicators, and more particularly, to laparoscopic surgical clip applicators.

Recently, surgical clips have been developed for use in the effective and efficient closing of surgical wounds. The use of such clips in place of, for example, sutures, staples, tapes, adhesives, sealants, and the like decreases overall surgical procedure time and reduces the risk of post-operative infection. These clips are described in U.S. Patent Application Publication No. 2013/0289586, the entirety of which is incorporated herein by reference.

It is desirable to provide applicators for these and other types of surgical clips that enable simple and efficient application of the clips to the wound site in the patient's tissue.

BRIEF SUMMARY OF THE INVENTION

One preferred embodiment of the present invention relates to a surgical clip applicator comprising: a base housing including a body portion, a trigger movable with respect to the body portion, a cannula having a first end positioned within the body portion and an opposing second end, and a clip application mechanism extending within and through at least a portion of a length of the cannula. A portion of the second end of the cannula is configured to engage a clip to be applied to a patient's tissue. The clip application mechanism includes a first linkage movable with respect to the body portion and the cannula and a jaw rotatable about a pivot mount. A first actuation of the trigger causes the first linkage to be moved in a linear direction with respect to the body portion and the cannula and the jaw to be rotated in a first direction about the pivot mount, for placing the clip in an open position on the patient's tissue. A second actuation of the trigger causes the jaw to be rotated in second direction about the pivot mount, the second direction being opposite to the first direction, placing the clip in a closed position on the patient's tissue.

Another preferred embodiment of the present invention relates to a surgical clip applicator comprising: a base housing including a body portion, a trigger movable with respect to the body portion, a cannula having a first end positioned within the body portion and an opposing second end, and a clip application mechanism extending within and through at least a portion of a length of the cannula. A portion of the second end of the cannula is configured as a first jaw to engage a clip to be applied to a patient's tissue. The clip application mechanism includes a first linkage movable with respect to the body portion and the cannula and a second linkage movable with respect to the body portion and the cannula. The second linkage has a first end rotatable about a first pivot mount and an opposing second end, and a second jaw for engaging the clip provided at the second end and being rotatable about a second pivot mount. A first actuation of the trigger causes the second linkage to be rotated in a first direction about the first pivot mount, and the second jaw to be rotated in a second direction about the second pivot mount, the second direction being opposite to the first direction, to place the clip in an open position. A second actuation of the trigger causes the second linkage to be rotated in the second direction about the first pivot mount and the second jaw to be rotated in the first direction about the second pivot mount to place the clip in a closed position on the patient's tissue.

BRIEF DESCRIPTION OF THE DRAWINGS

The following detailed description of preferred embodiments of the invention will be better understood when read in conjunction with the appended drawings. For the purpose of illustration, there are shown in the drawings embodiments which are presently preferred. It should be understood, however, that the invention is not limited to the precise arrangements and instrumentalities shown.

DETAILED DESCRIPTION OF THE INVENTION

Figure 1:
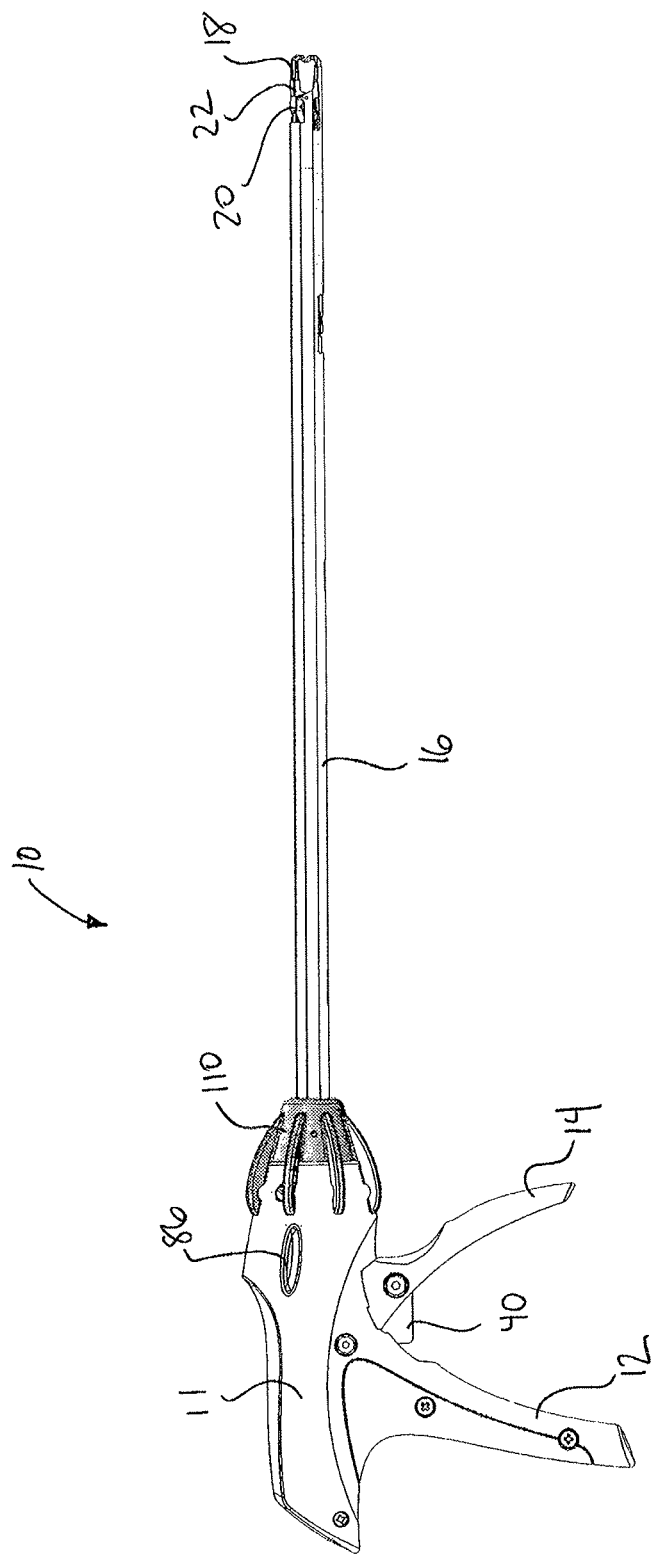
FIG. 1 is a right side elevational view of a surgical clip applicator in accordance with a first preferred embodiment of the present invention.

Certain terminology is used in the following description for convenience only and is not limiting. The words "right", "left", "lower", and "upper" designate directions in the drawings to which reference is made. The words "inwardly" and "outwardly" refer to directions toward and away from, respectively, the geometric center of the device and designated parts thereof. The terminology includes the above-listed words, derivatives thereof, and words of similar import. Additionally, the words "a" and "an" mean "at least one."

Referring to the drawings in detail, there is shown in FIGS. 1-6 a first preferred embodiment of a surgical clip applicator 10. The applicator 10 preferably has a gun-style base housing including a body portion 11, a handle grip 12 extending from the body portion 11, a trigger 14 extending from and movable with respect to the body portion 11 proximate the handle grip 12, and a cannula 16 extending from within the body portion 11 in a direction generally perpendicular to the handle grip 12. While the configuration of the applicator 10 shown in the drawings is preferred, other configurations may be used as well. Components of the applicator 10 described herein may be made from medical grade polymeric material, surgical steel, or like materials or combinations thereof.

The applicator 10 is used to position, ready, and apply one or more surgical clips 18 from a distal end of the cannula 16 to tissue of a patient (not shown) for closing wounds. The clip 18 applied by the applicator 10 is preferably that shown and described in U.S. 2013/0289586, and therefore further details of the structure and use of the clip 18 will not be described herein. However, embodiments of the present invention may be utilized with other types of surgical clips as well.

Figure 2:
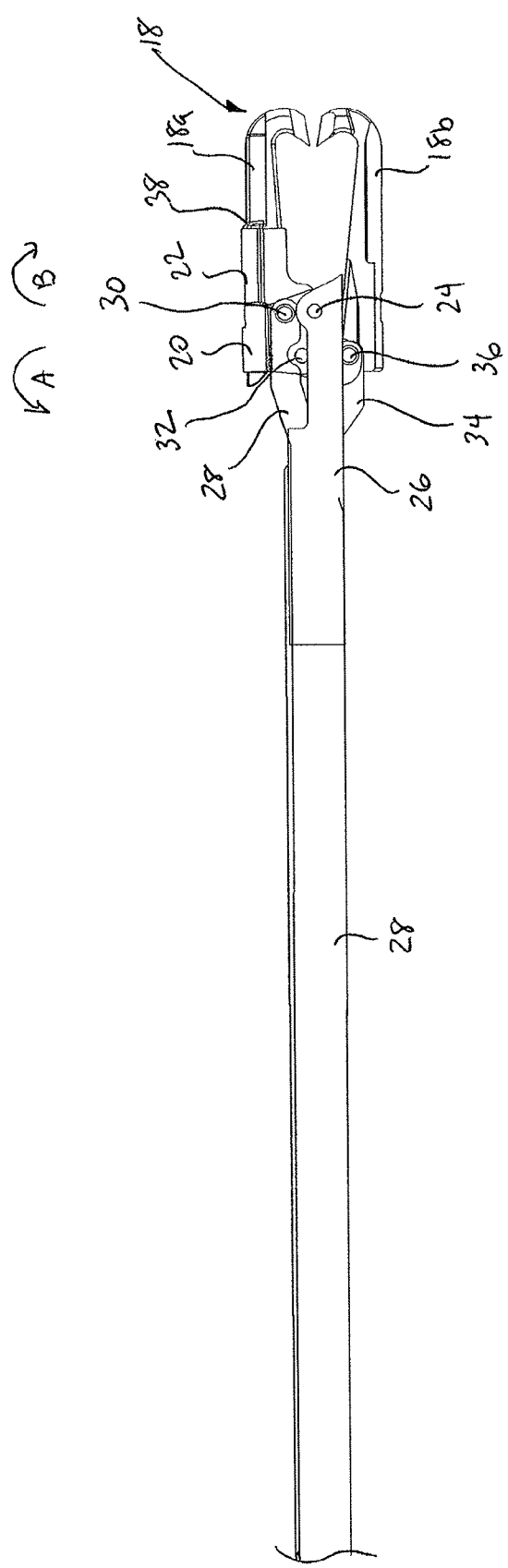
FIG. 2 is an enlarged right side elevational view of a surgical clip disposed within jaws and linkages of the surgical clip applicator of FIG. 1.

It is preferred that up to five clips 18 may be stored in the cannula 16 of the applicator 10 at one time for use. However, the cannula 16 and/or the applicator 10 may be designed to have a higher or lower clip storage limit, as desired. The clips 18 are preferably stored in the cannula 16 in an initial storage position (e.g., wherein proximal ends of first and second clip arms 18a, 18b only partially engage one another or do not engage one another, as described in U.S. 2013/0289586), with at least a portion of the distal-most clip 18 protruding from the distal end of the cannula 16, as shown in FIG. 2.

The second arm 18b of the clip 18 may be supported by an inner surface of the cannula 16. It is preferred that the first arm 18a of the clip 18 be disposed within one of the first and second pivotable jaws 20, 22 arranged at the distal end of the cannula 16 and shaped to receive the clip 18. For example, FIG. 2 shows a first jaw 20 and a second jaw 22 mounted distally of the first jaw 20. The first jaw 20 is mounted to the cannula 16 (not shown in FIG. 2) and a pair of opposing distal brackets 26 by first pivot mounts 24 (it being noted that only one distal bracket 26 and first pivot mount 24 are visible in FIG. 2). The first pivot mount 24 may be by way of a pin or the like. A pair of first linkages 28 (one visible in FIG. 2) are preferably pivotally coupled to the first jaw 20 at second pivot mounts 30 located above the first pivot mounts 24. The first linkages 28 preferably extend through the length of the cannula 16 and into the body portion 11 of the applicator 10 for actuation via the trigger 14. As will be described in further detail below, initial motion of the trigger 14 pulls the first linkages 28 proximally (i.e., toward the body portion 11), which via the coupling at the second pivot mounts 30 causes rotation of the first jaw 20 about the first pivot mounts 24 in the direction A shown in FIG. 2. The first jaw 20 therefore exerts pressure on a proximal end of the clip 18, causing the first and second clip arms 18a, 18b to engage one another through a pin (not shown) at the proximal ends thereof, while distal ends of the first and second clip arms 18a, 18b move away from one another into an open position (as described in U.S. 2013/0289586).

The second jaw 22 is preferably rotatably mounted to the first jaw 20 at a pair of third pivot mounts 32 (only one visible). In a preferred embodiment, the second jaw 22 is free to "float" with rotation of the first jaw 20 as described above. That is, when the first jaw 20 is rotated in direction A during the initial trigger 14 pull, the second jaw 22 does not necessarily rotate therewith. However, it is understood that contact with the first clip arm 18a during opening of the clip 18 may also cause rotation of the second jaw 22 in the direction A.

The second jaw 22 is also rotatably coupled to a pair of second linkages 34 (one visible) that extend through the length of the cannula 16 and into the body portion 11 of the applicator 10 for actuation via the trigger 14. The second linkages 34 are preferably located radially inwardly from the first linkages 28 and are preferably slidable with respect to the first linkages 28 for independent actuation. The second linkages 34 are coupled to the second jaw 22 via a pair of fourth pivot mounts 36, which are preferably located below the third pivot mounts 32. As will be described in further detail below, continued motion of the trigger 14 (i.e., after the above described initial motion which pulls the first linkage 28 proximally) pulls the second linkages 34 proximally (i.e., toward the body portion 11), which via the coupling at the fourth pivot mounts 36 causes rotation of the second jaw 22 about the third pivot mounts 32 in the direction B shown in FIG. 2, which is opposite to direction A. The second jaw 22 therefore exerts pressure on a distal end of the clip 18, causing the distal ends of the first and second clip arms 18a, 18b to come together to a closed position on the surgical wound in the tissue (as described in U.S. 2013/0289586).

The second jaw 22 preferably further includes a pair of tabs 38 downwardly depending from an upper surface of the second jaw 22. The tabs 38 preferably engage an abutment surface (not shown) of the clip 18 when the clip is in the storage and open positions. The tabs 38 aid in retaining the clip 18 within the cannula 16 for completion of application. Once the clip 18 is in the closed position and the second jaw 22 is released to its original position shown in FIG. 2, the tab 38 preferably are no longer in engagement with the abutment surface of the clip 18 and the cannula 16 can be withdrawn, leaving the clip 18 behind at the surgical site to close off the surgical wound.

Figure 3:
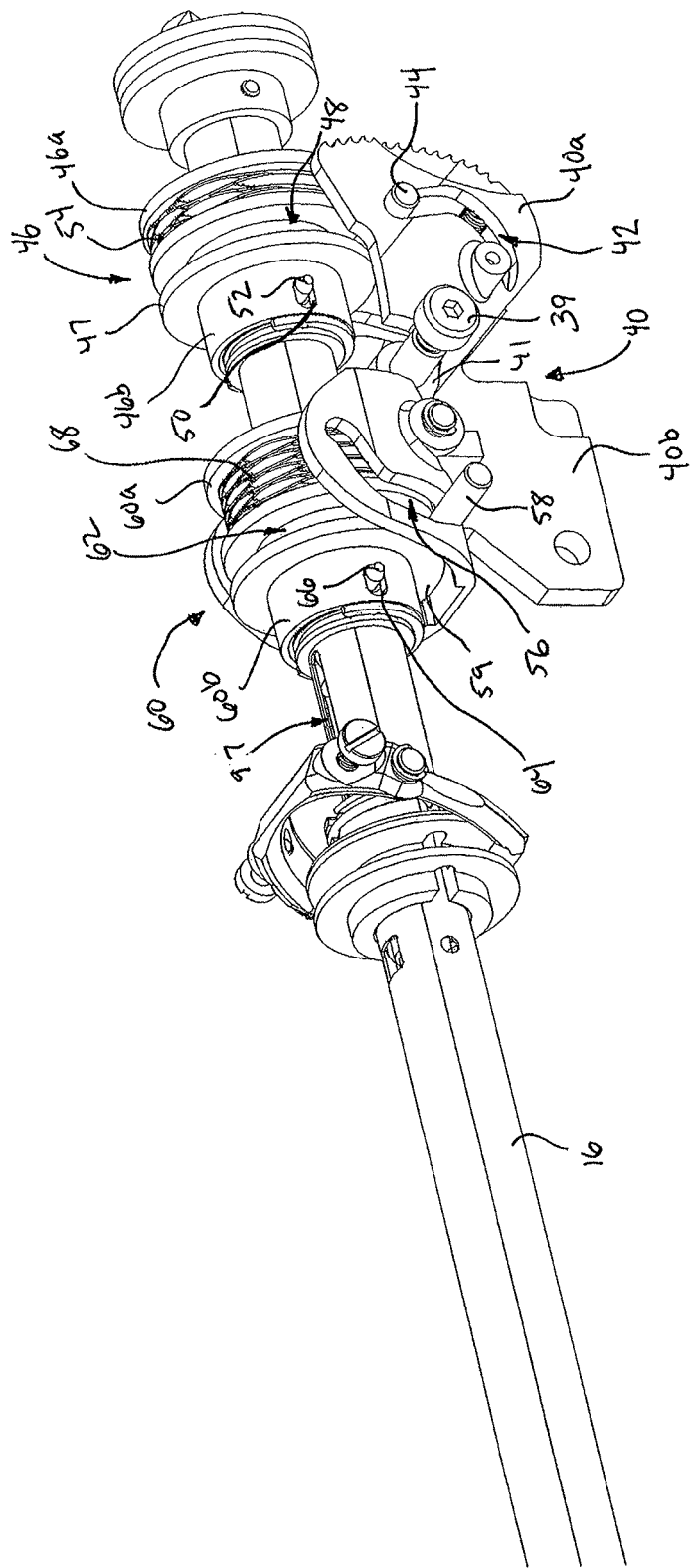
FIG. 3 is an enlarged left side perspective view of components of the surgical clip applicator of FIG. 1 for moving the linkages.
Figure 4:
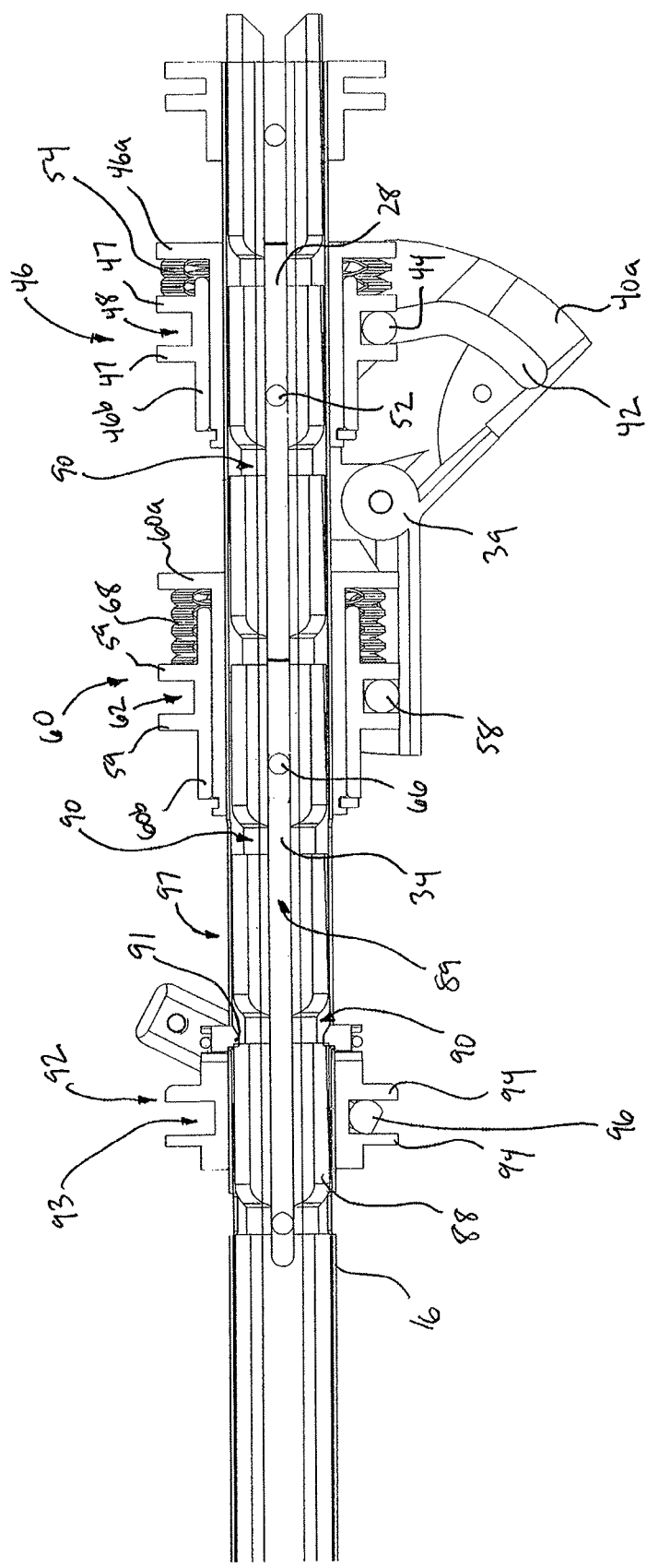
FIG. 4 is an enlarged left side elevational cross-sectional view of the components of FIG. 3.
Figure 5:
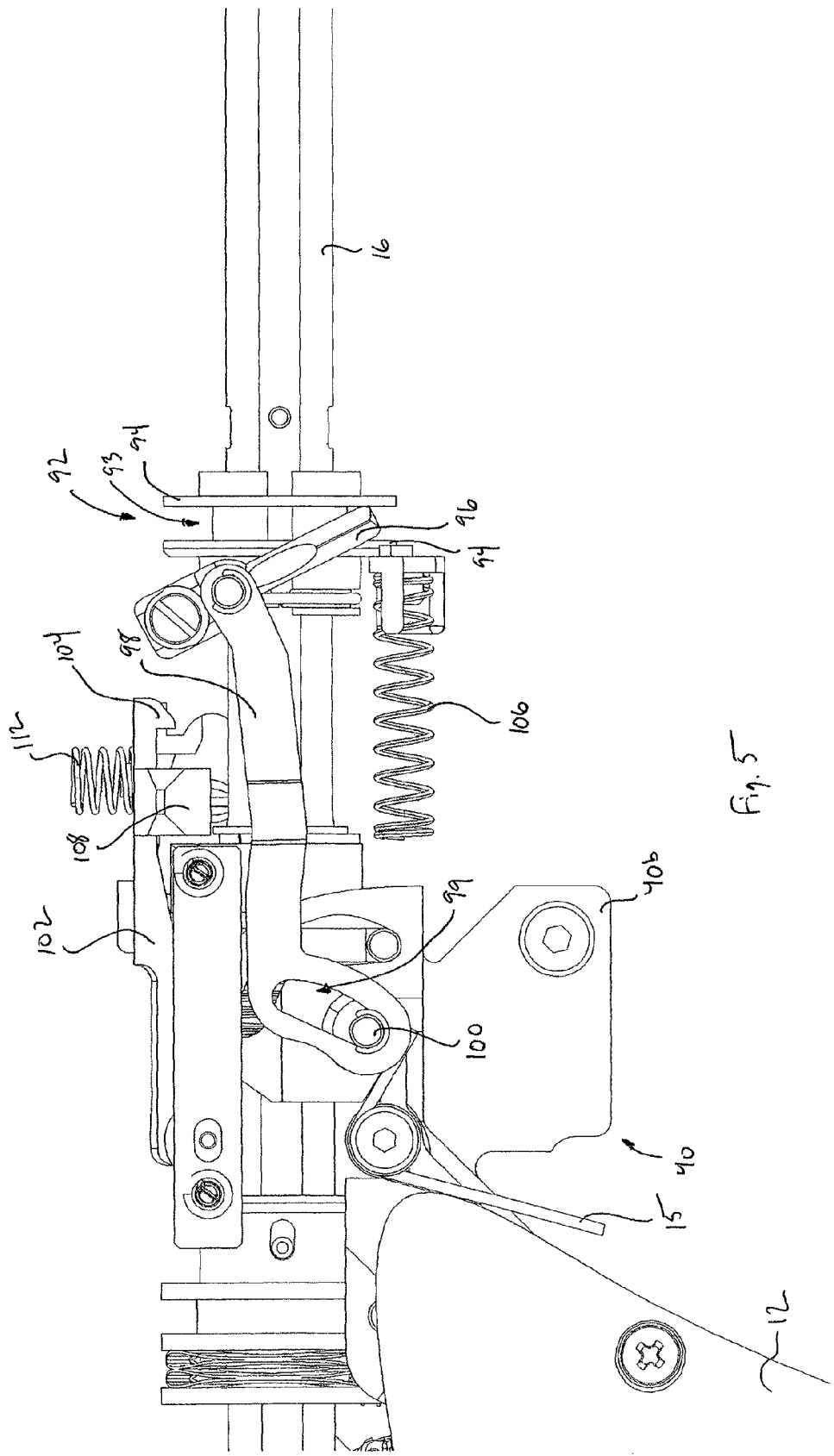
FIG. 5 is an enlarged right side elevational view of a clip advancement mechanism of the surgical clip applicator of FIG. 1.

Referring specifically to FIGS. 3 and 4, actuation of the first and second linkages 28, 34 for rotating the first and second jaws 20, 22 is driven by pulling of the trigger 14 toward the handle grip 12. Attached to the trigger 14 (see e.g., FIG. 1) is a cam plate 40. The cam plate 40 preferably includes a proximal portion 40a and a distal portion 40b and is rotatable with respect to the body portion 11 through actuation of the trigger 14. For example, the cam plate 40 may have a mounting channel 41 disposed between the proximal and distal portions 40a, 40b through which one or more attachment bolts 39 may be arranged to couple the cam plate 40 and the body portion 11. The trigger 14 and cam plate 40 may be spring biased to the initial position with respect to the body portion 11, as shown in FIGS. 1, 3, and 4, by one or more torsion springs 15 (see FIG. 5).

The proximal portion 40a of the cam plate 40 preferably includes a pair of first grooves 42 that receive a first handle drive pin 44 therethrough. The first grooves 42 are sized and shaped such that through rotation of the cam plate 40, the first handle drive pin 44 is moved proximally with respect to the body portion 11, at least during a first portion of the trigger 14 pull. The first handle drive pin 44 preferably also interacts with a first retainer ring 46, which includes an inner stationary portion 46a fixed to the cannula 16 and an outer portion 46b which is slidably arranged on a surface of the inner portion 46a. The outer portion 46b of the first retainer ring 46 includes a channel 48 that preferably extends around an entire radial periphery of the outer portion 46b and is formed by a pair of spaced apart, generally radially outwardly extending flanges 47. The first handle drive pin 44 preferably rests within the channel 48 of the first retainer ring 46 and during rotation of the cam plate 40, moves the outer portion 46b of the first retainer ring 46 proximally with respect to the inner portion 46a through interaction of the first handle drive pin 44 with one of the flanges 47.

The first retainer ring 46 preferably radially surrounds a portion of the cannula 16 and portions of the first linkages 28 located within the cannula 16. The first retainer ring 46 preferably includes one or more, and preferably a pair, of pin slots 50 that are aligned with openings (not shown) in the first linkages 28 and the cannula 16. A first axial drive pin 52 extends through the pin slots 50 in the first retainer ring 46, as well as through the corresponding openings in the first linkages 28 and the cannula 16. As the outer portion 46b of the first retainer ring 46 is moved proximally by the first handle drive pin 44, edges of the pin slots 50 therein contact and move the first axial drive pin 52 proximally as well. The first axial drive pin 52 accordingly moves the first linkages 28 proximally within the cannula 16 to cause the aforementioned rotation of the first jaw 20.

A first force-limiting spring 54 is preferably placed between the inner and outer portions 46a, 46b of the first retainer ring 46, in particular in a radially surrounding part of the inner portion 46a and abutting one of the flanges 47 of the outer portion 46b. The first force-limiting spring 54 limits the amount of input force exerted on the first linkages 28, and therefore the first jaw 20, so as to avoid damage to components of the applicator 10 and/or to the clip 18. In a preferred embodiment, the first force-limiting spring 54 limits the force on opening the clip 18 to about fifty Newtons (N).

The distal portion 40b of the cam plate 40 preferably includes a pair of second grooves 56 that receive a second handle drive pin 58 therethrough. The second grooves 56 are sized and shaped such that through rotation of the cam plate 40, the second handle drive pin 58 is moved proximally with respect to the body portion 11, at least during a second, subsequent portion of the trigger 14 pull. In particular, the shapes of the second grooves 56 preferably allow for the second handle drive pin 58 to remain in its original position with respect to the cannula 16 during the initial portion of the trigger 14 pull, and only after the clip 18 has been opened, does the shape of the grooves 58 slope to provide for proximal motion of the second handle drive pin 58. The second handle drive pin 58 preferably also interacts with a second retainer ring 60, which is constructed much like the first retainer ring 46, i.e., including cooperating inner and outer portions 60a, 60b. The outer portion 60b of the second retainer ring 60 includes a channel 62 that preferably extends around an entire radial periphery of the outer portion 60b and is formed by a pair of flanges 59. The second handle drive pin 58 preferably rests within the channel 62 of the second retainer ring 60 and during rotation of the cam plate 40, moves the outer portion 60b of the second retainer ring 60 proximally with respect to the inner portion 60a through interaction of the second handle drive pin 58 with one of the flanges 59.

Similar to the first retainer ring 46, the second retainer ring 58 preferably radially surrounds a portion of the cannula 16 and portions of the first and second linkages 28, 34 located within the cannula 16. The second retainer ring 60 preferably includes pin slots 64 that are aligned with openings (not shown) in the first and second linkages 28, 34 and the cannula 16. A second axial drive pin 66 extends through the pin slots 64 in the second retainer ring 60, as well as through the corresponding openings in the first and second linkages 28, 34 and the cannula 16. As the outer portion 60b of the second retainer ring 60 is moved proximally by the second handle drive pin 58, edges of the pin slots 64 therein contact and move the second axial drive pin 66 proximally as well. The second axial drive pin 66 accordingly moves the second linkages 34 proximally within the cannula 16 to cause the aforementioned rotation of the second jaw 22.

A second force-limiting spring 68 is preferably placed between the inner and outer portions 60a, 60b of the second retainer ring, in particular in a radially surrounding part of the inner portion 60a and abutting one of the flanges 59 of the outer portion 60b. In a preferred embodiment, the second force-limiting spring 68 limits the force on closing the clip 18 to about ninety N.

Figure 6:
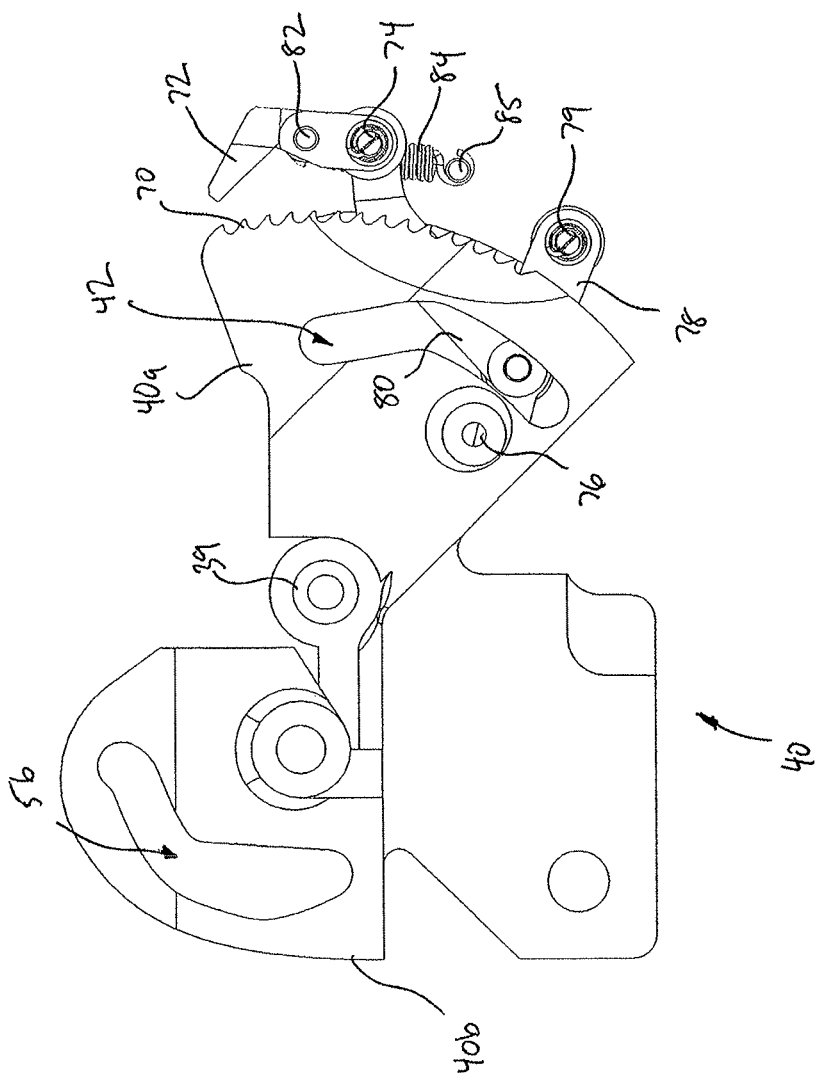
FIG. 6 is an enlarged left side elevational view of a trigger lock mechanism of the surgical clip applicator of FIG. 1.

Since the clips 18 for use with the applicator 10 often undergo plastic deformation during application, it can be important to prevent reversal of the application process. In a preferred embodiment, once the user of the applicator 10 initiates pulling the trigger 14, the clip 18 application process must be completed before the trigger 14 can be released to its original position. For example, FIG. 6 shows a mechanism for locking the trigger 14 in place during a trigger 14 pull and preventing release of the trigger 14 prior to completion of clip 18 application. One of the proximal edges of the proximal portion 40a of the cam plate 40 may include a plurality of teeth 70 that interact with a pawl 72. As the trigger 14 is pulled and the cam plate 40 rotates, the pawl 72 may sequentially engage each tooth 70 to prevent the cam plate 40, and thus the trigger 14, from moving back to its original position.

The pawl 72 is preferably rotatably mounted to the body portion 11 via a bolt 74 or the like. A cross-bar 76 is further preferably attached to the cam plate 40, via press-fit, adhesive, mechanical fastener, or the like, for movement therewith. The cross-bar 76 abuts a first pawl link 78 which is rotatably mounted at one end to the body portion 11 via a bolt 79 or the like. Between the bolt 79 and the abutment to the cross-bar 76, the first pawl link 78 is rotatably coupled to one end of a second pawl link 80. An opposite end of the second pawl link 80 is attached to the pawl 72 via an arm 82, which couples to the pawl 72 above the bolt 74 mounting the pawl 72 to the body portion 11.

With this configuration, as the cam plate 40 rotates during pull of the trigger 14, the pawl 72 rotates along an angled side of each tooth 70 on the cam plate 40 to pass, although if the motion of the trigger 14 is disrupted, the pawl 72 locks onto the nearest tooth 70 to prevent return of the cam plate 40. As completion of the trigger 14 pull is neared, the cross-bar 76 rotates the first pawl link 78 about the bolt 79 coupled to the body portion 11, which in turn forces the second pawl link 80 proximally, and the arm 82 rotates the pawl 72 away from the teeth 70 on the cam plate 40. This allows the cam plate 40 to rotate back into its original position following proper application of the clip 18. The arm 82 is preferably connected to one end of a spring 84, the other end of which is attached to a post 85 connected to the body portion 11. The spring 84 biases the arm 82, and the pawl 72, to a position where the pawl 72 can engage the teeth 70 on the cam plate 40.

As described above, the applicator 10 preferably can store a plurality of clips 18 in the cannula 16 at one time. The applicator 10 therefore preferably includes a mechanism for advancing the clips 18 within the cannula 16 after the distal-most clip 18 is applied to a surgical wound. For example, referring to FIGS. 1, 4, and 5, a push button 86 may be provided that allows the user to manually advance the clips 18 within the cannula 16.

The most proximally-located clip 18 in the cannula 16 preferably abuts an end of a magazine rod 88 that is slidably disposed within the cannula 16. However, a spring (not shown) or other device may be disposed between the end of the magazine rod 88 and the clip 18. Movement of the magazine rod 88 in the distal direction forces the abutting clip 18, and any other clips 18 located in the cannula 16 to also move in the distal direction. The magazine rod 88 preferably includes a central slit 89 which allows the first and second axial drive pins 52, 66 to pass therethrough.

The magazine rod 88 further includes, on an outer radial peripheral surface thereof, a plurality of notches 90 which are axially spaced apart from one another by a distance corresponding to an axial length of a clip 18. During operation, one of the notches 90 is engaged by a rib 91 of a rod retainer ring 92 that radially surrounds the cannula 16 and is slidable with respect thereto. The cannula 16 includes an opening 97 through which the rib 91 extends to engage a notch 90 of the magazine rod 88. The rod retainer ring 92 includes a channel 93 that preferably extends around an entire radial periphery of the rod retainer ring 92 and is formed by a pair of spaced apart flanges 94. A portion of a bracket 96 rests within the channel 93 and is rotatably connected to a pair of cam arms 98 (only one visible in FIG. 5). Each cam arm 98 includes a groove 99 that engages a magazine pin 100 that extends through and is movable with the cam plate 40.

As the cam plate 40 rotates during a trigger 14 pull, the magazine pin 100 moves with the cam plate 40 and within the groove 99 of the cam arm 98, pulling the bracket 96 proximally. The bracket 96 consequently moves the rod retainer ring 92 proximally such that rib 91 is moved from one of the notches 90 of the magazine rod 88 to an adjacent, proximally-located notch 90. As the rod retainer ring 92 moves proximally, it also passes a hook 104 of a lever arm 102 mounted to the body portion 11. Following completion of the trigger 14 pull and application of the clip 18, the lever arm 102 retains the rod retainer ring 92 in a proximal position by engaging the hook 104 with one of the flanges 94 of the rod retainer ring 92. During proximal movement of the rod retainer ring 92, a pair of loading springs 106 (one visible in FIG. 5) disposed between a flange 94 of the rod retainer ring 92 and the body portion 11 (not shown in FIG. 5) are compressed, and bias the rod retainer ring 92 toward a distal position shown in FIG. 5. However, the hook 104 of the lever arm 102 prevents distal motion of the rod retainer ring 92 prior to a time selected by the user.

To release the hook 104, the lever arm 102 is provided with a ramped cam surface 108 that extends toward the push button 86. When the user wishes to advance the clips 18 within the cannula 16, the push button 86 is pressed, which engages a portion thereof against the cam surface 108 of the lever arm 102, forcing the lever arm 102 and the hook 104 upwardly and away from the flange 94 of the rod retainer ring 92. The loading spring 106 forces the rod retainer ring 92 distally, which through engagement with a notch 90 of the magazine rod 88 advances the magazine rod 88 distally as well by a length of one clip 18, thereby moving the next clip 18 into position within the first and second jaws 20, 22. A spring 112 coupled to the body portion 11 at one end and to the lever arm 102 at the other end biases the lever arm 102 back to its original position for retaining the rod retainer ring 92.

The applicator 10 further preferably includes a rotation sleeve 110 that is fixed to and radially surrounds a portion of the cannula 16. By rotating the rotation sleeve 110, the cannula 16, as well as the first and second jaws 20, 22, the first and second retainer rings 46, 60, the rod retainer ring 92, the first and second linkages 28, 34, and the first and second axial drive pins 52, 66 can all be rotated with respect to the body portion 11 and handle grip 12. In this way, the first and second jaws 20, 22 may be positioned in any orientation without having to turn or adjust the body portion 11 and handle grip 12. The circular configuration of the channels 48, 62, 97 in the respective first and second retainer rings 46, 60 and the rod retainer ring 92 all allow rotation thereof without having to move the first and second handle drive pins 44, 58 or the magazine pin 100.

Referring to FIGS. 7-15, there is shown a second preferred embodiment of a surgical clip applicator 200. Similar to the applicator 10 of FIGS. 1-6, the applicator 200 preferably has a gun-style base housing 210 including a body portion 211, a handle grip 212 extending from the body portion 211, a trigger 214 extending from and movable with respect to the body portion 211 proximate the handle grip 212, and a cannula 216 extending from within the body portion 211 in a direction generally perpendicular to the handle grip 212. While the configuration of the applicator 200 shown in the drawings is preferred, other configurations may be used as well. In particular, a configuration which does not utilize a trigger 214 may be utilized. Components of the applicator 200 described herein may be made from medical grade polymeric material, surgical steel, or like materials or combinations thereof.

Similar to the applicator 10 of FIGS. 1-6, the applicator 200 is used to position, ready, and apply one or more surgical clips 218 from a distal end 216b of the cannula 216 to tissue of a patient (not shown) for closing wounds. The clip 218 applied by the applicator 200 is preferably that shown and described in US 2013/0289586, and therefore further details of the structure and use of the clip 218 will not be described herein. However, embodiments of the present invention may be utilized with other types of surgical clips as well. The applicator 200 of FIGS. 7-15 includes the same or a similar ratchet and pawl mechanism for locking the trigger 214 in place during a trigger 214 pull and preventing release of the trigger 214 prior to completion of clip 218 application, as that described with respect to the applicator 10 of FIGS. 1-6.

Figure 7:
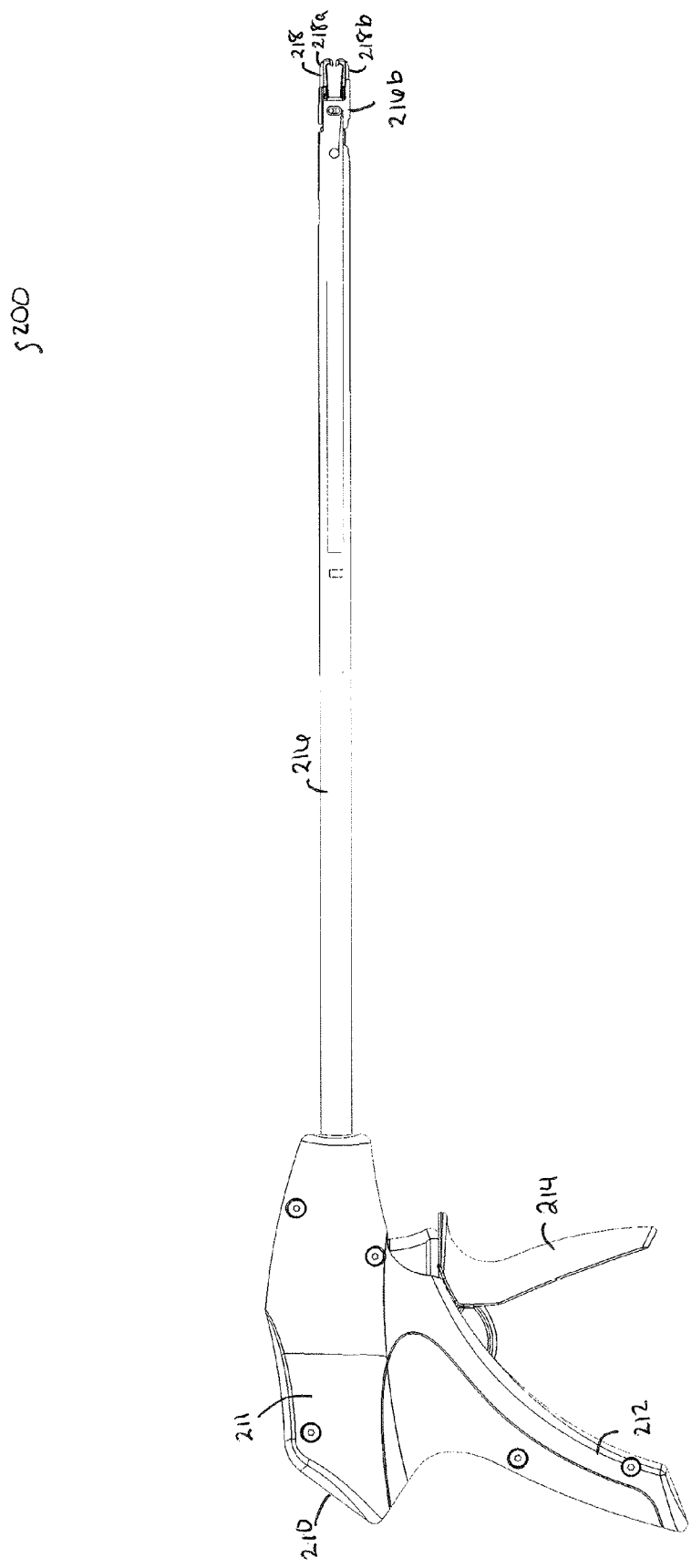
FIG. 7 is a right side elevational view of a surgical clip applicator in accordance with a second preferred embodiment of the present invention.
Figure 9:
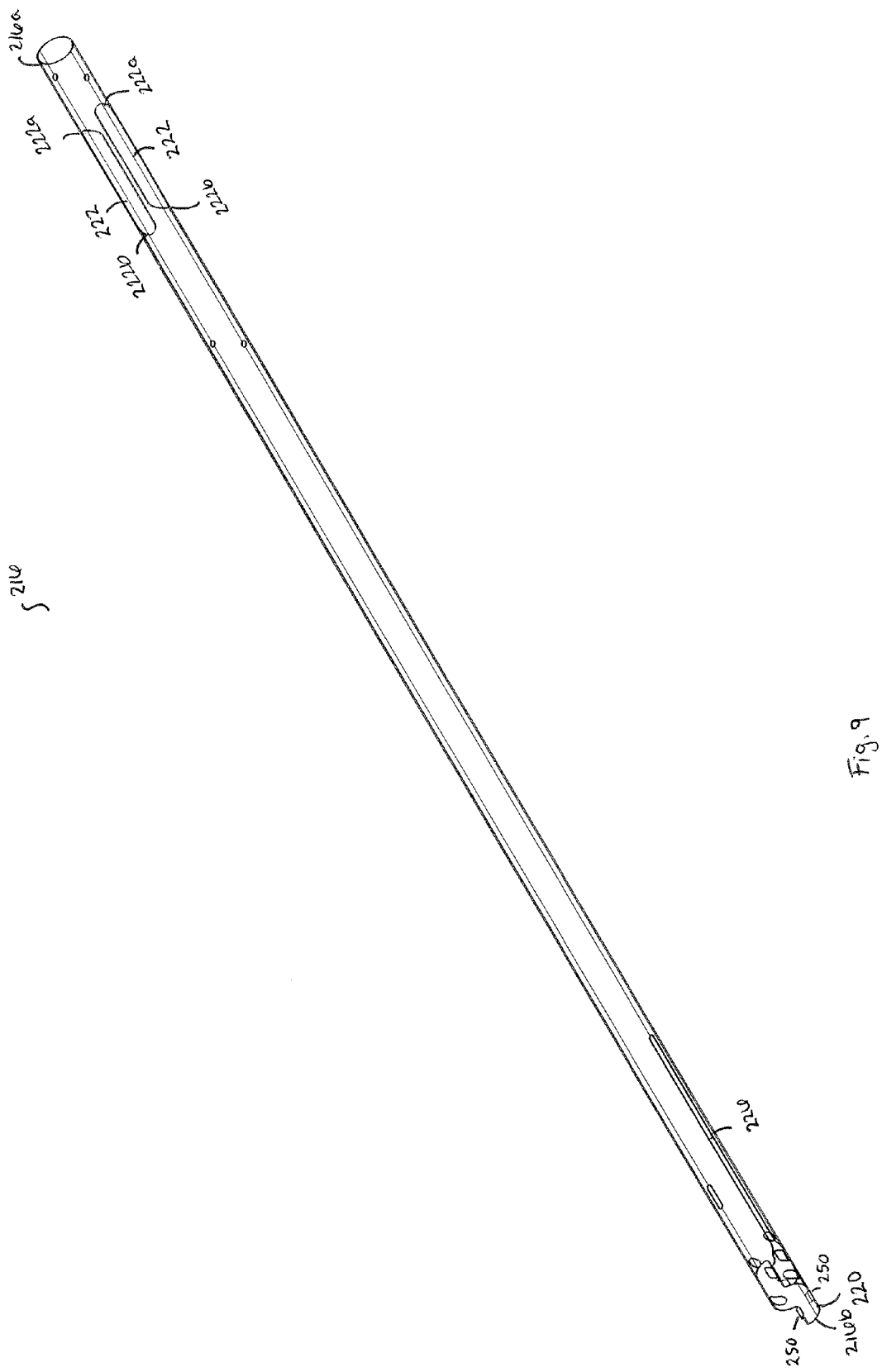
FIG. 9 is a left side perspective view of a cannula of the surgical clip applicator of FIG. 7.

In use, a single clip 218 is positioned at or grasped by the distal end 216b of the cannula 216, such that at least a portion of the clip 218 protrudes from the distal end 216b of the cannula 216. Either the first or second arm 218a, 218b of the clip 218 may be supported by an inner surface of the cannula 216, and more particularly by a stationary jaw 220 formed at the distal end 216b of the cannula 216, as shown in FIGS. 7 and 9. The stationary jaw 220 forms a bottom jaw for storage and application of the clip 218. The other of the first and second arms 218a, 218b of the clip 218 is disposed within a pivoting jaw 224 (FIG. 12) shaped to receive the clip 218, as will be described in further detail herein. The pivoting jaw 224 forms a top jaw for storage and application of the clip 218.

Figure 10:
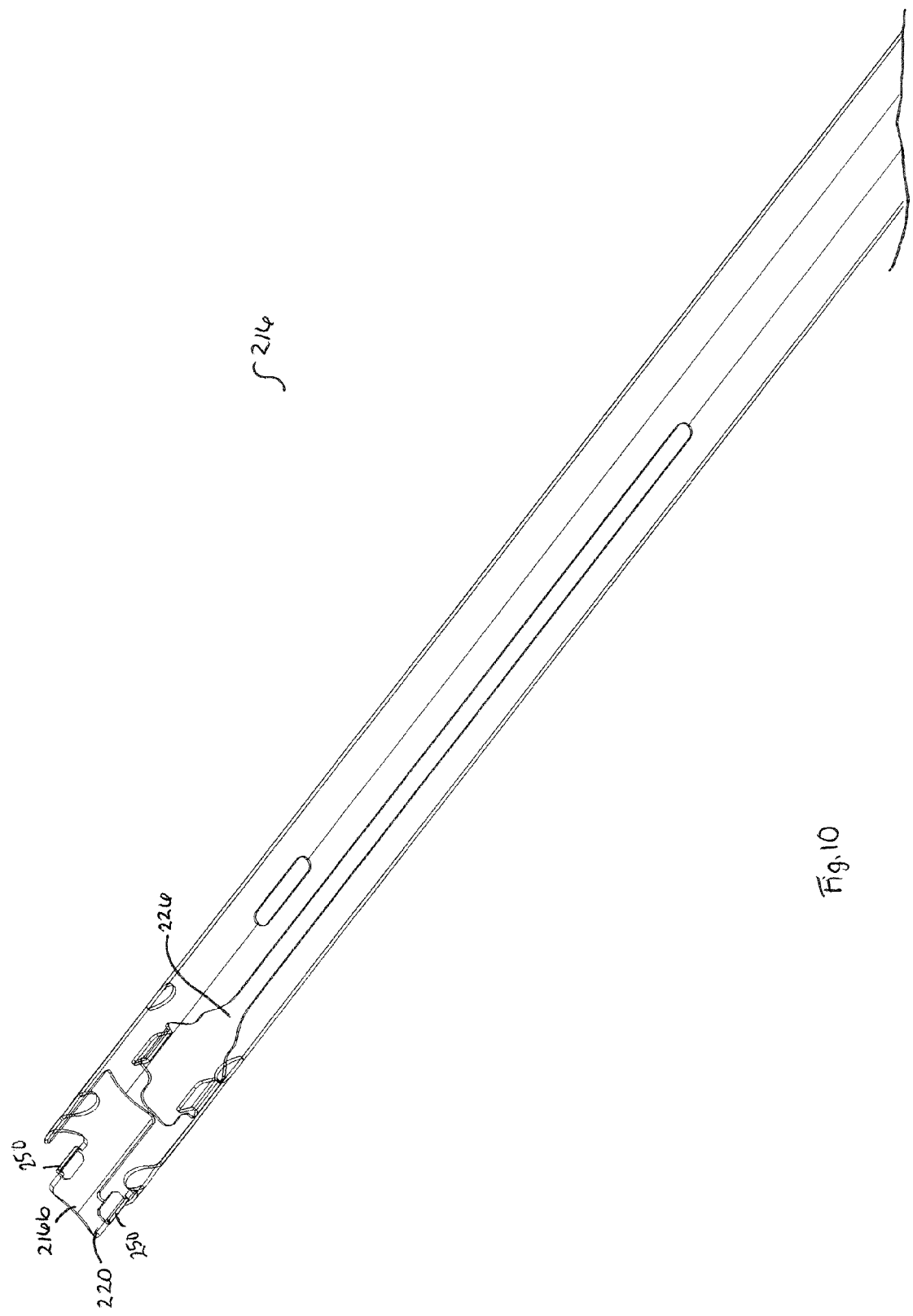
FIG. 10 is an enlarged left side perspective view of a distal end of the cannula of FIG. 9.

A proximal or rear end 216a of the cannula 216 is positioned within, and more particularly extends into, the body portion 211 of the base housing 210. The proximal end 216a of the cannula 216 preferably includes a pair of first elongated grooves or slots 222 (one shown in FIG. 8 but both shown in FIG. 9) formed in opposing surfaces of the proximal end 216a of the cannula 216 at corresponding positions. Referring to FIGS. 9-10, a second elongated groove or slot 226 is formed in a bottom surface of the cannula 216, and more particularly in a surface of the cannula 216 that is generally 90° from the surfaces in which the first elongated slots 222 are formed. The second elongated slot 226 is formed proximate the distal end 216b of the cannula 216, and more particularly the second elongated slot 226 extends from a position proximate the distal end 216b toward the proximal end 216a.

Figure 11:
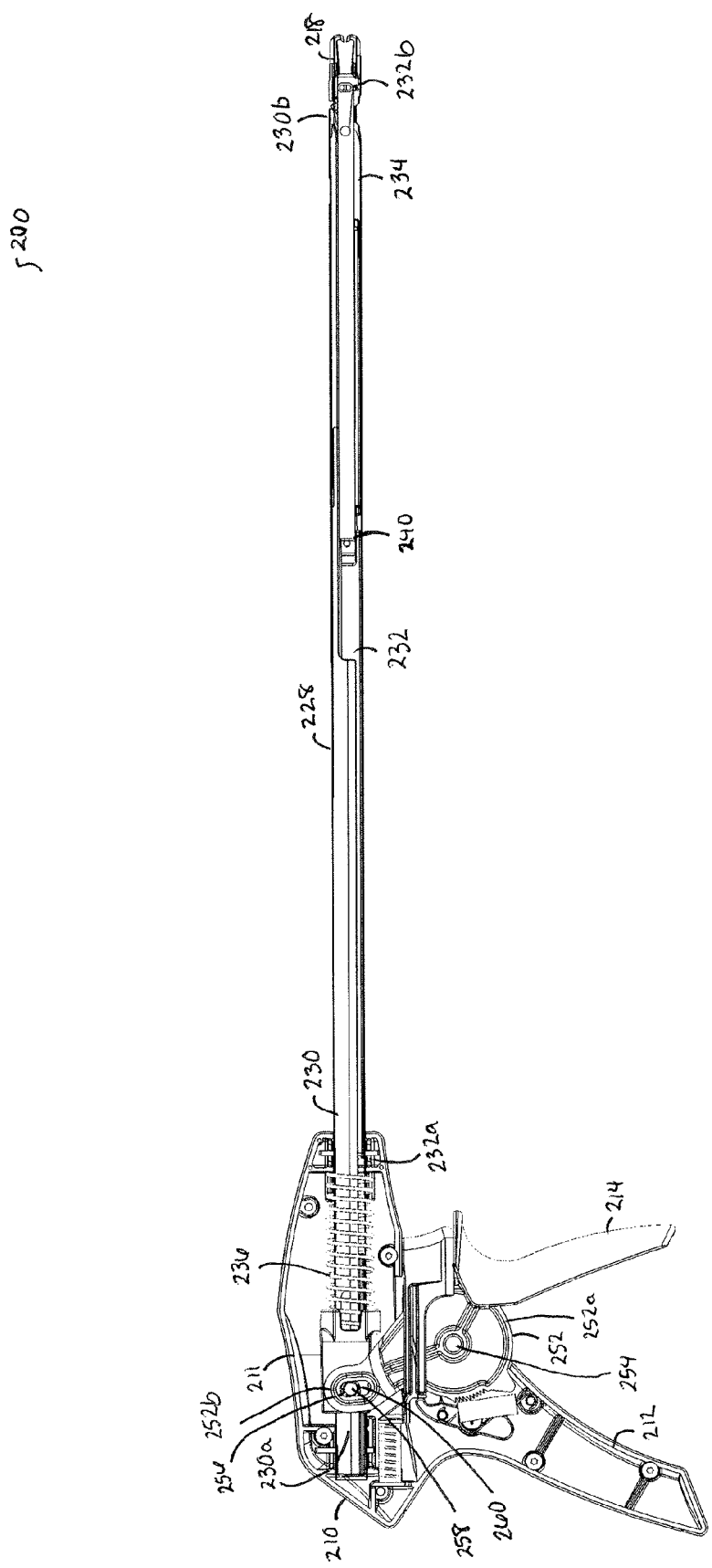
FIG. 11 is a right side elevational view of the surgical clip applicator of FIG. 7 with a portion of the outer housing and the cannula omitted.
Figure 12:
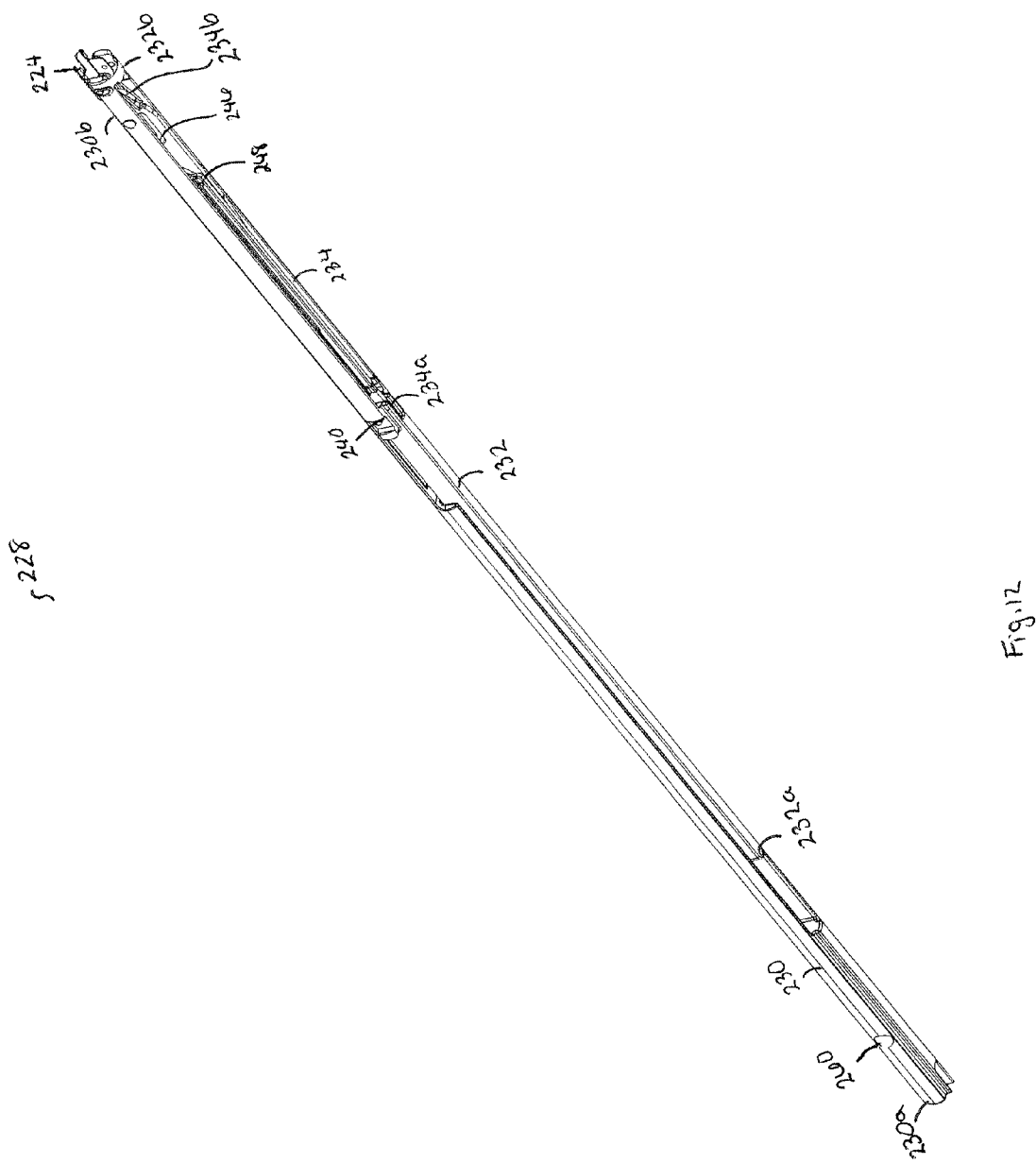
FIG. 12 is a right side perspective view of a clip application mechanism of the surgical clip applicator of FIG. 7.

As shown in FIG. 11, in which the cannula 216 has been omitted for illustrative purposes, a clip application mechanism 228 is preferably provided within an interior of the cannula 216 and extends along at least a portion of a length of the cannula 216 from its proximal end 216a to its distal end 216b. Referring to FIGS. 11-12, the clip application mechanism 228 includes a first linkage 230 extending from the body portion 211 proximate the handle grip 212 and movable with respect to the body portion 211 and the cannula 216, a lower frame 232 fixedly secured within the cannula 216, and a second linkage 234 extending from and pivotably secured to the lower frame 232.

The first linkage 230 is caused to move, and more particularly slide, with respect to the base housing 210 upon actuation by the trigger 214. Preferably, a spring 236 is disposed between a proximal end 230a of the first linkage 230, which extends into the body portion 211 of the base housing 210, and interior components of the body portion 211, such that the first linkage 230 is spring-loaded relative to the base housing 210. A length of the first linkage 230 extends from the proximal end 230a to an opposing distal end 230b. More particularly, the first linkage 230 preferably extends through the length of the cannula 216 and into the body portion 211 of the applicator 200 for actuation via the trigger 214.

Figure 13:
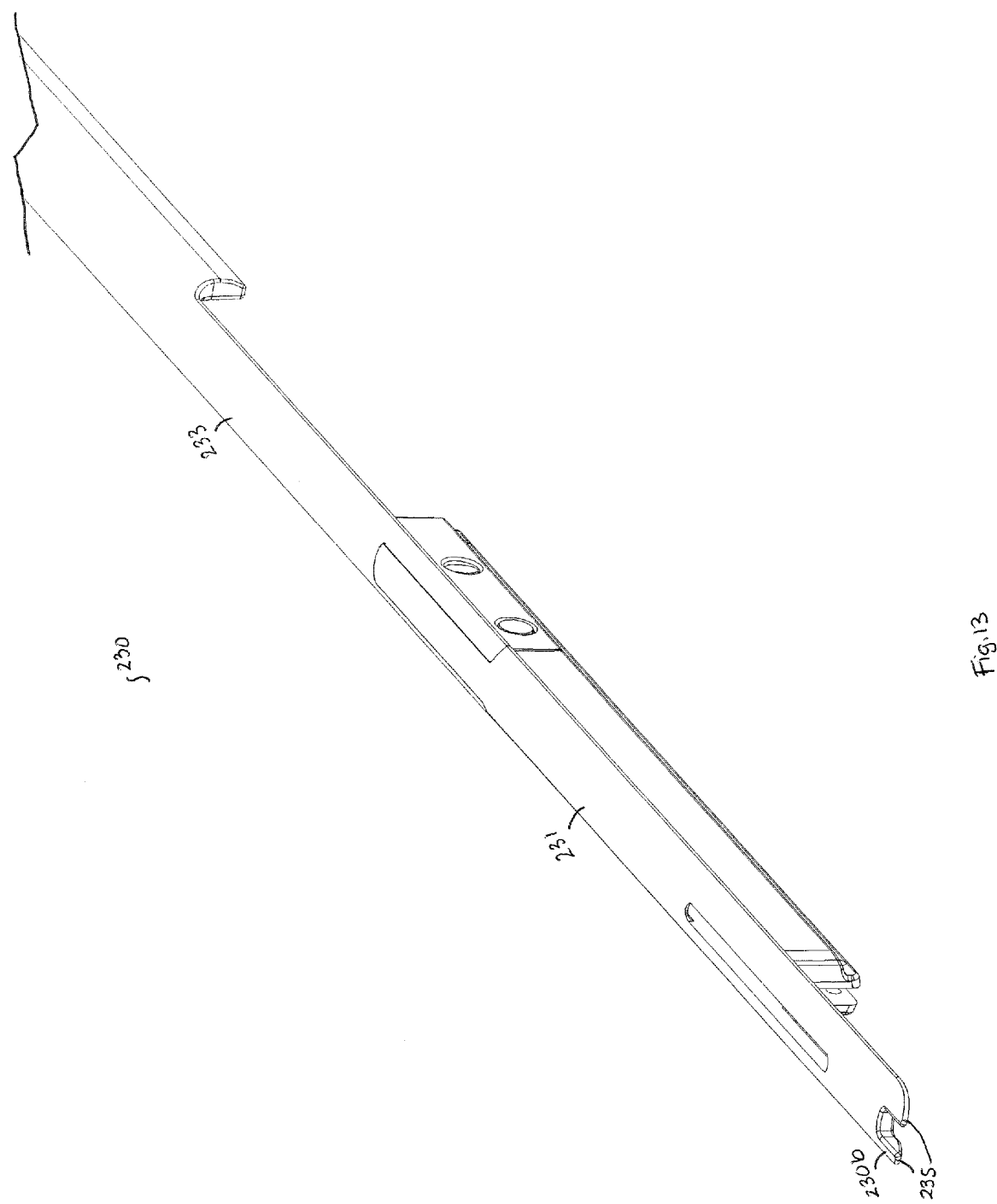
FIG. 13 is an enlarged left side perspective view of a distal end of a first linkage of the clip application mechanism of FIG. 12.

In one embodiment, as shown in FIG. 13, the first linkage 230 is formed by two separate members 231, 233 secured together by one or more pins (not shown). However, it will be understood that other configurations may be used as well. For example, the first linkage 230 may be formed as a unitary body. The distal end 230b of the first linkage 230 is formed as a U-shaped structure configured to engage and facilitate ejection of a clip 218 from the applicator upon closure of the clip 218. More particularly, after closure of the clip 218 on a patient's tissue, which is primarily facilitated by the second linkage 234 as will be described in further detail herein, and more preferably almost immediately after closure of the clip 218 on the patient's tissue, the U-shaped distal end 230b of the first linkage 230 comes into contact with the closed clip 218 and pushes or otherwise urges the closed clip 218 out of the applicator 200. Preferably, the tips 235 of the U-shaped distal end 230b interact with or otherwise contact a portion of the compression pin (not shown) extending outside of the first and second arms 218a, 218b of the clip 218.

Figure 14:
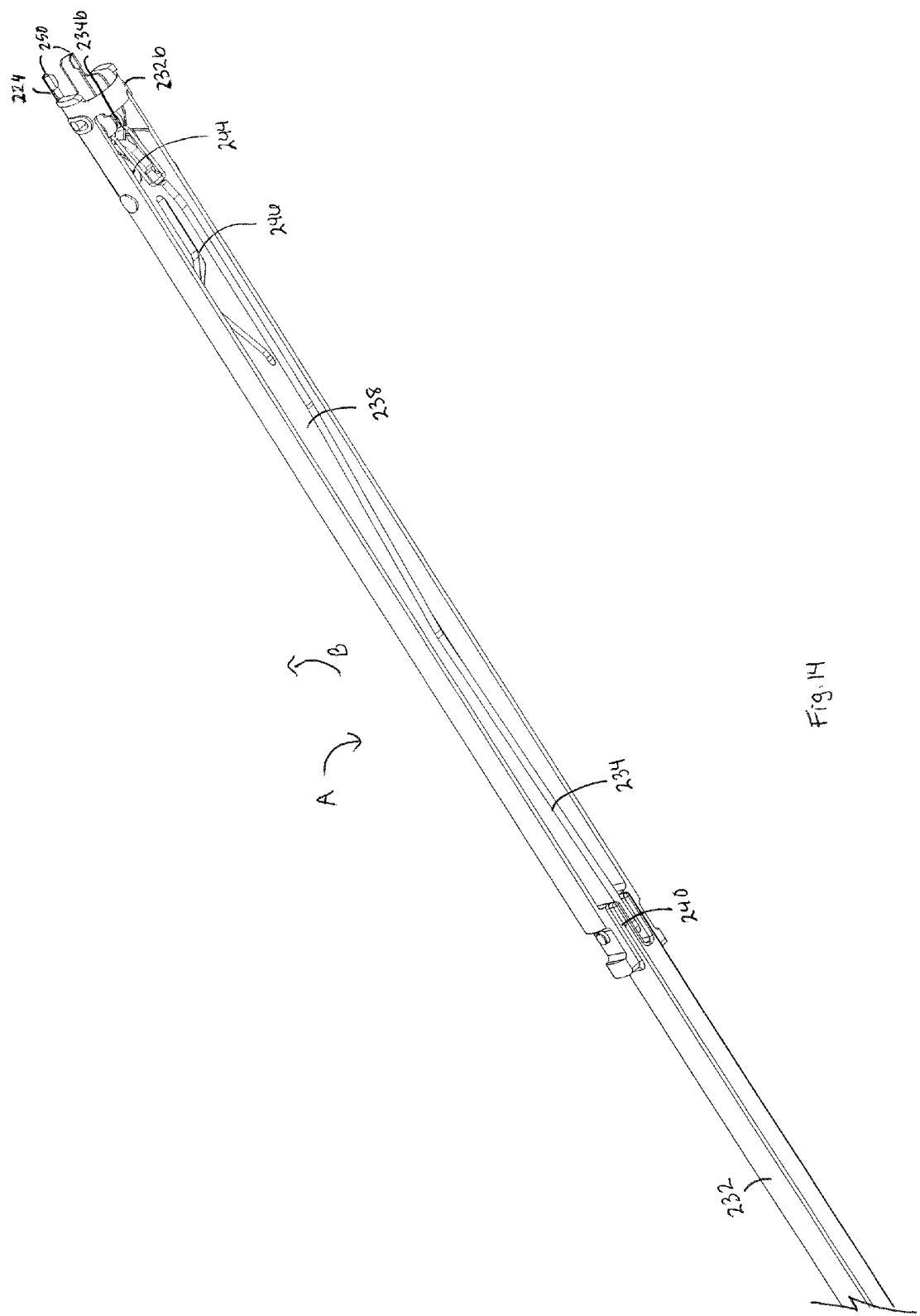
FIG. 14 is an enlarged right side perspective view of a portion of a lower frame and a second linkage of the clip application mechanism of FIG. 12.

Referring to FIGS. 11-12 and 14, a length of the lower frame 232 extends from the proximal end 232a to an opposing distal end 232b. More particularly, the lower frame 232 extends through a portion of the length of the cannula 216 and into the body portion 211 of the applicator 200, with the proximal end 232a of the lower frame 232 being disposed proximate a distalmost tip of the body portion 211.

Figure 15:
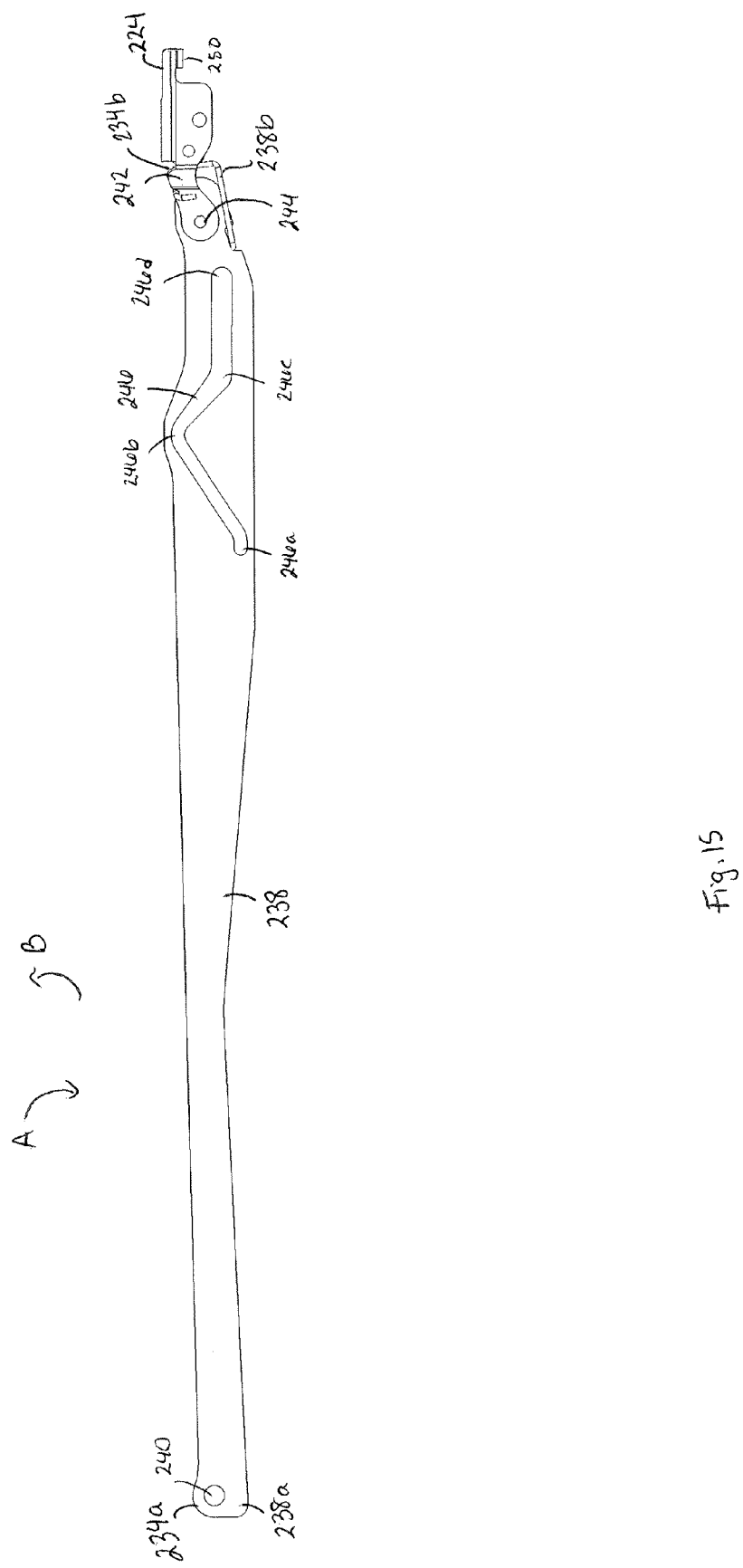
FIG. 15 is an enlarged right side elevational view of a second linkage of the clip application mechanism of FIG. 12.

As shown, for example, in FIG. 14, the second linkage 234 is preferably formed radially inwardly of the lower frame 232. Referring to FIG. 15, the second linkage 234 includes a bar 238 mounted to the lower frame 232 by a first pivot mount 240 at or near a first, proximal end 234a of the second linkage 234. A pivoting jaw 224 is coupled to the pivoting bar 238 at a second, distal end 234b of the second linkage 234. More particularly, the pivoting jaw 224 is coupled or mounted to the pivoting bar 238 by a pair of opposing brackets 242 about a second pivot mount 244 (it being noted that only one bracket 242 is visible in FIG. 15), such that the jaw 224 can rotate about the second pivot mount 244. The first and second pivot mounts 240, 244 may be by way of a pin or the like. The first pivot mount 240 is provided at a proximal end 238a of the pivoting bar 238, while the pivoting jaw 224 is formed at an opposing distal end 238b of the pivoting bar 238.

As best shown in FIG. 15, the pivoting bar 238 further includes a non-linear groove or slot 246 formed proximate its distal end 238b and the pivoting jaw 224. The non-linear slot 246 essentially is shaped as an inverted "V." More particularly, the non-linear slot 246 extends from a first end 246a in a generally upward direction to an apex 246b, then in a generally downward direction to a second end 246d which is proximate the distal end 238b of the pivoting bar 238. More preferably, the non-linear slot 246 extends in the generally downward direction from the apex 246b to an intermediate point 246c and finally in a generally linear manner to the second end 246d. An interior surface of the slidable first linkage 230 includes a slot pin 248 (see FIG. 12) configured to be received in and move along the non-linear slot 246 of the pivoting bar 238.

As shown in FIGS. 9-10 and 14-15, the stationary and pivoting jaws 220, 224 preferably each includes a pair of protrusions 250 extending in a curved manner from opposing lateral side surfaces of each jaw 220, 224 to engage corresponding grooves formed in the first and second arms 218a, 218b of the clip 218 when the clip 218 is in the open position. The curved protrusions 250 aid in retaining the clip 218 at the distal end 216b of the cannula 216 for completion of application.

Referring to FIGS. 8-15, actuation of the first and second linkages 230, 234, for example for rotating the pivoting jaw 224 to place the applicator 200 in a ready position to accept a clip 218 for application, is driven by pulling of the trigger 214 toward the handle grip 212. Attached to the trigger 214 (see e.g., FIG. 8) is a cam plate 252. The proximal end 230a of the first linkage 230 is in communication with the trigger 214 via the cam plate 252. The cam plate 252 preferably includes a first portion 252a proximate the handle grip 212 and a second portion 252b distal from the handle grip 212. The cam plate 252 is rotatable with respect to the body portion 211 through actuation of the trigger 214. For example, the cam plate 252 may have a mounting channel 254 disposed in the first portion 252a through which one or more attachment bolts may be arranged to couple the cam plate 252 and the body portion 211 and about which the cam plate 252 may rotate with respect to the body portion 211. The trigger 214 and cam plate 252 may be spring biased to the initial position with respect to the body portion 211 by one or more springs.

Figure 8:
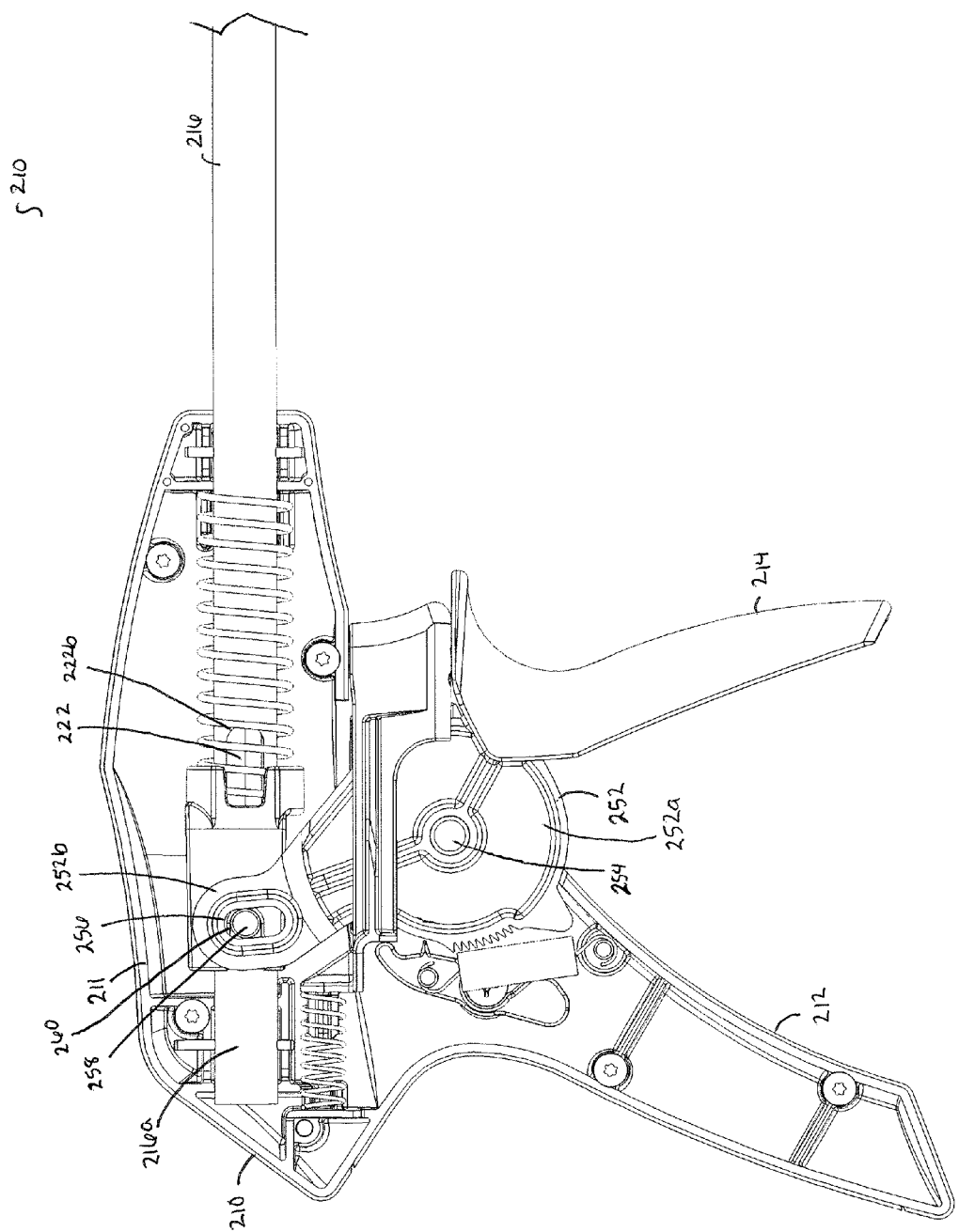
FIG. 8 is an enlarged right side elevational view of a portion of a clip advancement mechanism of the surgical clip applicator of FIG. 7 with a portion of an outer housing omitted.

The second portion 252b of the cam plate 252 preferably includes a pair of openings 256 (it being noted that only one is shown in FIGS. 8 and 11) that receive a first axial drive pin 258 therethrough. The first axial drive pin 258 also extends through corresponding openings 260 formed in the proximal end 230a of the first linkage 230, such that the first linkage 230 and the cam plate 252 are fixedly secured together and rotation of the cam plate 252 caused by actuation of the trigger 214 also causes movement of the first linkage 230.

As shown in FIG. 8, the elongated slots 222 of the cannula 216 are aligned with the corresponding and respective openings 256, 260 formed in the cam plate 252 and the first linkage 230. As such, the first axial drive pin 258 also extends through the elongated slots 222 formed in the proximal end 216a of the cannula 216. More particularly, elongated slots 222 are sized and shaped such that the first axial drive pin 258 rests within and is configured to move along the elongated slots 222 upon actuation of the trigger 214.

Initial motion of the trigger 214 is caused by a first or partial actuation of the trigger 214 (i.e., a first or partial trigger 214 pull). The first actuation of the trigger 214 causes a first or partial rotation of the cam plate 252. By the partial or first rotation of the cam plate 252, the first axial drive pin 258 and the first linkage are moved in a linear manner with respect to the body portion 211 and the cannula 216. More particularly, by the partial or first rotation of the cam plate 252, the first axial drive pin 258 is moved distally (i.e., away the body portion 211) with respect to the body portion 211 from a first end 222a of the elongated slots 222 toward a second end 222b of the elongated slots 222. As the first axial drive pin 258 is moved distally, the first linkage 230 is also moved, and more particularly pushed or slid, distally.

The distal movement of the first linkage 230 causes the interior slot pin 248 to travel along the non-linear slot 246 of the pivoting bar 238 of the second linkage 234, and more particularly from the first end 246a of the non-linear slot 246 toward the apex 246b. As the slot pin 248 approaches and ultimately reaches the apex 246b of the non-linear slot 246, the pivoting bar 238 of the second linkage 234 is caused to rotate or pivot in a first direction A about the coupling at the first pivot mount 240, such that the pivoting bar 238 extends through and outside of the lower frame 232 and through the elongated slot 226 formed in the bottom surface of the cannula 216. In turn, the pivoting jaw 224 rotates or pivots in a second direction B (opposed to the first direction) about the coupling at the second pivot mount 244. In such a position, the pivoting jaw 224 and the stationary jaw 220 are in an open position. Via the engagement between the curved protrusions 250 of the jaws 220, 224 and the grooves formed in the proximal end of the first and second clip arms 218a, 218b, the clip 218 is also placed in an open position by the partial actuation of the trigger 214.

To accomplish application of the clip 218 to a patient's tissue, the applicator 200 provided with the open clip 218 is positioned over the patient's tissue followed by continued motion of the trigger 214. The continued motion of the trigger 214 causes a second or complete actuation of the trigger 214. The second actuation of the trigger 214 causes two sequential actions to occur, namely closure of the clip 218 followed by ejection of the closed clip 218 from the applicator 200.

More particularly, the second actuation of the trigger 214 causes a second or complete rotation of the cam plate 252. By the complete rotation of the cam plate 252, the first axial drive pin 258 is moved further distally with respect to the body portion 211 to the a second end 222b of the elongated slots 222 which, in turn pushes the first linkage 230 further distally. The further distal movement of the first linkage 230 causes the interior slot pin 248 to travel further along the non-linear slot 246 of the pivoting bar 238 of the second linkage 234, and more particularly from the apex 246b in a downward direction toward the intermediate point 246c and ultimately to the second end 246d.

As the slot pin 248 travels in a downward direction to the intermediate point 246c and ultimately reaches the second end 246d of the non-linear slot 246, the pivoting bar 238 of the second linkage 234 is causes to rotate or pivot in the second direction B about the first pivot mount 240, such that the pivoting bar 238 moves upwardly through the elongated slot 226 in the bottom of the cannula 216 and to be housed within the lower frame 232. In turn, the pivoting jaw 224 rotates or pivots in the first direction A about the coupling at the second pivot mount 244. The pivoting jaw 224 exerts pressure on an intermediate point between the proximal and distal ends of the clip 218 or on the distal end of the clip 218, causing the distal ends of the first and second clip arms 218a, 218b to come together to a closed position on the surgical wound in the tissue (as described in U.S. 2013/0289586). Thus, in a first portion of the second actuation of the trigger 214, the clip 218 is placed in the closed position on the patient's tissue.

Subsequently, and more preferably almost immediately after closure of the clip 218 in the first portion of the second actuation, the closed clip 218 is ejected from the applicator 200 in a second portion of the second actuation of the trigger 214. More particularly, at or near the end of the second (or complete) actuation of the trigger 214, the distally-positioned first linkage 230 contacts the closed clip 218. More particularly, the tips 235 of the distal end 230b of the first linkage 230 engages the portions of the compression pin (not shown) extending outside of the first and second clip arms 218a, 218b to push or eject the clip 218 from applicator 200. Upon release of the trigger 214, the first axial drive pin 258 and the slot pin 248 are automatically biased back to their respective starting positions. The applicator 200 can then be withdrawn, leaving the clip 218 behind at the surgical site to close off the surgical wound.

From the foregoing, it can be seen that embodiments of the present invention comprise a surgical clip applicator. It will be appreciated by those skilled in the art that changes could be made to the embodiments described above without departing from the broad inventive concepts thereof. It is understood, therefore, that the invention is not limited to the particular embodiments disclosed, but it is intended to cover modifications within the spirit and scope of the present invention as defined by the appended claims.

We claim:

1. A surgical clip applicator comprising:
a base housing including a body portion;
a trigger movable with respect to the body portion;
a cannula having a first end positioned within the body portion and an opposing second end, a portion of the second end being configured as a first jaw to engage a clip to be applied to a patient's tissue, and
a clip application mechanism extending within and through at least a portion of a length of the cannula, the clip application mechanism including:
a first linkage movable with respect to the body portion and the cannula,
a second linkage movable with respect to the body portion and the cannula, the second linkage having a first end rotatable about a first pivot mount and an opposing second end and a second jaw for engaging the clip provided at the second end, the second jaw being rotatable about a second pivot mount, and
a lower frame having a first end and an opposing second end and a longitudinal axis extending therebetween, the second linkage being pivotably coupled to the lower frame about the first pivot mount and being formed radially inwardly of the lower frame with respect to the longitudinal axis of the lower frame, wherein a first actuation of the trigger causes the second linkage to be rotated in a first direction about the first pivot mount, and the second jaw to be rotated in a second direction about the second pivot mount, the second direction being opposite to the first direction, to place the clip in an open position, and wherein a second actuation of the trigger causes the second linkage to be rotated in the second direction about the first pivot mount and the second jaw to be rotated in the first direction about the second pivot mount to place the clip in a closed position on the patient's tissue.

2. The surgical clip applicator of claim 1, wherein a second end of the first linkage is configured to engage and cause ejection of the clip from the applicator after the clip has been placed in the closed position.

3. The surgical clip applicator of claim 1, wherein each of the first and second jaws includes at least one protrusion configured to engage corresponding grooves formed in first and second arms of the clip.

4. The surgical clip applicator of claim 1, wherein the second linkage includes a non-linear slot extending in a generally upward direction from a first end to an apex and in a generally downward direction from the apex to a second end.

5. The surgical clip applicator of claim 4, wherein the first linkage includes a slot pin movable within the non-linear slot.

6. The surgical clip applicator of claim 5, wherein the first actuation of the trigger causes the first linkage to be moved distally in a linear direction with respect to the body portion and causes the slot pin to move from the first end to the apex of the non-linear slot, such that the second linkage is rotated in the first direction about the first pivot mount and the second jaw is rotated in the second direction about the second pivot mount.

7. The surgical clip applicator of claim 6, wherein the second actuation of the trigger causes the slot pin to move from the apex to the second end of the non-linear slot of the second linkage, such that the second linkage is rotated in the second direction about the first pivot mount and the second jaw is rotated in the first direction about the second pivot mount.

8. The surgical clip applicator of claim 1, further comprising a cam plate rotatable with respect to the body portion and having a first portion attached to the trigger and a second portion attached to the first linkage.

9. The surgical clip applicator of claim 8, further comprising a first pair of openings formed in the cam plate, a second pair of openings formed in the first linkage and an axial drive pin extending through the first and second pair of openings to secure the first linkage to the cam plate.

10. The surgical clip applicator of claim 9, further comprising a pair of elongated slots formed in the cannula, the axial drive pin being movable within the elongated slots upon actuation of the trigger.

11. The surgical clip applicator of claim 10, wherein the first and second actuations of the trigger cause the axial drive pin and the first linkage to be moved distally with respect to the body portion.

12. A surgical clip applicator comprising:
a base housing including a body portion;
a trigger movable with respect to the body portion;
a cannula having a first end positioned within the body portion and an opposing second end, a portion of the second end being configured as a stationary first jaw to engage a clip to be applied to a patient's tissue, and
a clip application mechanism extending within and through at least a portion of a length of the cannula, the clip application mechanism including:
a first linkage movable with respect to the body portion and the cannula, and
a second linkage movable with respect to the body portion and the cannula, the second linkage having a first end rotatable about a first pivot mount and an opposing second end and a second jaw for engaging the clip provided at the second end, the second jaw being rotatable about a second pivot mount, and
a lower frame having a first end and an opposing second end and a longitudinal axis extending therebetween, the second linkage being pivotably coupled to the lower frame about the first pivot mount and being formed radially inwardly of the lower frame with respect to the longitudinal axis of the lower frame,
wherein a first actuation of the trigger causes the second linkage to be rotated in a first direction about the first pivot mount, and the second jaw to be rotated in a second direction about the second pivot mount, the second direction being opposite to the first direction, to place the clip in an open position, and
wherein a second actuation of the trigger causes the second linkage to be rotated in the second direction about the first pivot mount and the second jaw to be rotated in the first direction about the second pivot mount to place the clip in a closed position on the patient's tissue.

* * * * *